(12) United States Patent
Zhong et al.

(10) Patent No.: US 6,635,078 B1
(45) Date of Patent: Oct. 21, 2003

(54) COATED STENTS WITH BETTER GRIPPING ABILITY

(75) Inventors: Sheng-Ping Zhong, Northborough, MA (US); Steven A. Schultz, Northborough, MA (US); Kristian J. Dimatteo, Waltham, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 195 days.

(21) Appl. No.: 09/667,916

(22) Filed: Sep. 22, 2000

(51) Int. Cl.⁷ .................................................. A61F 2/06
(52) U.S. Cl. ........................ 623/1.11; 606/108; 606/194
(58) Field of Search ........................... 623/1.11, 11.11, 623/1.23; 606/108, 191, 192, 194, 195, 198; 604/96.01, 523

(56) References Cited

U.S. PATENT DOCUMENTS

| | | | |
|---|---|---|---|
| 4,921,483 A * | 5/1990 | Wijay et al. ............ 604/102.02 |
| 5,100,429 A | 3/1992 | Sinofsky et al. ............ 606/195 |
| 5,211,654 A | 5/1993 | Kaltenbach ................. 606/191 |
| 5,556,383 A | 9/1996 | Wang et al. .................... 604/96 |
| 5,571,166 A * | 11/1996 | Dinh et al. .................. 128/898 |
| 5,624,450 A | 4/1997 | Glastra ........................ 606/108 |
| 5,643,278 A | 7/1997 | Wijay ......................... 606/108 |
| 5,766,201 A * | 6/1998 | Ravenscroft et al. ........ 606/108 |
| 5,836,965 A | 11/1998 | Jendersee et al. ............ 606/198 |
| 5,855,565 A | 1/1999 | Bar-Cohen et al. .......... 604/104 |
| 5,893,868 A | 4/1999 | Hanson et al. ............... 606/198 |
| 5,957,930 A | 9/1999 | Vrba ........................... 606/108 |
| 5,976,155 A | 11/1999 | Foreman et al. ............. 606/108 |
| 6,024,752 A | 2/2000 | Horn et al. ................... 606/192 |
| 6,033,433 A | 3/2000 | Ehr et al. ........................ 623/1 |
| 6,036,697 A | 3/2000 | DiCaprio ..................... 606/108 |
| 6,066,156 A | 5/2000 | Yan ............................. 606/192 |
| 6,187,013 B1 | 2/2001 | Stoltze et al. ................ 606/108 |
| 6,245,076 B1 | 6/2001 | Yan ............................. 606/108 |
| 6,306,144 B1 * | 10/2001 | Sydney et al. ............... 604/265 |
| 6,312,457 B1 * | 11/2001 | DiMatteo et al. ........... 623/1.13 |

* cited by examiner

Primary Examiner—Corrine McDermott
Assistant Examiner—Urmi Chattopadhyay
(74) Attorney, Agent, or Firm—Vidas, Arrett & Steinkraus

(57) ABSTRACT

A medical device delivery apparatus is provided which comprises a catheter having an expandable and contractible member and an expandable medical device disposed about the expandable and contractible member. At least portions of at least one of the medical device and the expandable and contractible member have a pressure sensitive adhesive applied thereto to adhere the medical device to the expandable and contractible member. The pressure sensitive adhesive is selected so as to release the medical device from the expandable and contractible member upon contraction of the member from an expanded state. Suitable medical devices include stents.

26 Claims, 2 Drawing Sheets

COATED STENTS WITH BETTER GRIPPING ABILITY

BACKGROUND OF THE INVENTION

The use of expandable stents and other prostheses is well known in the art. Typically, stents are placed in a vessel during or after an angioplasty procedure or other procedure to maintain the patency of a bodily vessel. While stents are often used in the circulatory system, they find use in other parts of the body as well including the urinary system.

Stents are generally mechanically expandable, self-expanding or hybrid—that is both mechanically expandable and self-expanding. A hybrid stent will generally self-expand to a certain diameter after which it is mechanically expanded to a larger diameter or opening. Mechanically expandable stents are usually expanded by the application of a radially outward force to the stent via an expansion device such as a balloon located within the stent.

In use, a stent is disposed about an expansion device such as a balloon at the distal end of a catheter. A portion of the catheter is inserted in a desired bodily vessel and advanced to a desired bodily location. The balloon or other expansion device is then expanded, thereby expanding the stent and implanting the stent at the desired bodily location. Subsequently, the balloon or other expansion device is contracted and withdrawn from the body, leaving the stent behind in the body.

Unfortunately, unless the stent is secured to the balloon or other expansion device, undesirable slipping or motion of the stent relative to the balloon or other expansion device may occur during delivery of the stent to the desired bodily location and during expansion of the stent. In order to prevent this, a number of approaches have been taken.

One approach involves crimping the stent tightly to the balloon. Care must be taken, however, to avoid puncturing the balloon and to avoid damaging the stent.

Another approach focuses on the choice of balloon materials to provide a more resilient balloon surface with less slippage of the stent relative to the balloon. More resilient balloon materials, however, may compromise non-compliance features of the balloon as well as the burst pressure of the balloon. Although the coextrusion of a base layer comprising a high strength material with a resilient top layer material has been considered, it is difficult to find compatible materials.

Yet another approach to preventing relative movement of the balloon and stent involves setting a balloon to the shape of a stent as been disclosed in U.S. Pat. No. 5,836,965 to Jendersee. The use of protrusions on a balloon to engage a stent has been disclosed in copending and commonly assigned U.S. application Ser. No. 09/283375. A stent may also be retained on a balloon via the use of sleeves or socks, as disclosed in copending and commonly assigned U.S. applications Ser. Nos. 09/407836 and 09/427805. Sleeves or socks typically overlay the ends of the stent.

Yet another approach involves the use of adhesives to glue the stent to the balloon. U.S. Pat. No. 5,100,429 discloses the use of a photodegradeable adhesive to attach a stent to an inflatable balloon. The balloon is held in place on the stent until ultraviolet energy is directed at the adhesive thereby freeing the stent from the balloon. The balloon is subsequently expanded to implant the stent.

The use of glue to secure a stent to a balloon is also disclosed in U.S. Pat. No. 5,643,278. As disclosed therein, the adhesive bond between the stent and the balloon breaks upon expansion of the balloon. Thus, once the balloon is expanded, relative motion between the stent and the balloon may occur. This may impede accurate positioning of the stent if, during expansion of the balloon, there has been any undesirable movement of the balloon away from the desired bodily location.

It is desirable to provide a stent which is adhered to a balloon prior to inflation of the balloon and following inflation of the balloon until the balloon is deflated, at which point, the stent releases from the balloon. By adhering the stent to the balloon until the balloon is deflated, the practitioner has the option, following inflation of the balloon but prior to deflation of the balloon, of adjusting the position of the stent in the body prior to release of the stent.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

BRIEF SUMMARY OF THE INVENTION

The present invention is directed in one embodiment to a medical device delivery apparatus comprising a catheter having an expandable and contractible member and an expandable medical device disposed about the expandable and contractible member. At least a portion of at least one of the medical device and the expandable and contractible member have a pressure sensitive adhesive applied thereto to adhere the medical device to the expandable and contractible member. The pressure sensitive adhesive is selected so as to release the medical device from the expandable and contractible member upon contraction of the member from an expanded state. Desirably, the medical device is a stent.

In another embodiment, the invention is directed to an expanded medical device disposed about an expanded expansion member on a catheter. The expanded medical device is adhered to the expanded expansion member via a pressure sensitive adhesive which releases upon contraction of the expansion member.

In yet another embodiment, the invention is directed to a method of delivering an expanded medical device to a desired bodily location comprising the steps of providing an inventive expanded medical device at a desired bodily location, contracting the expansion member thereby releasing the expanded medical device from the expansion member and withdrawing the expansion member and catheter from the body, the expanded medical device remaining at the desired bodily location.

In another embodiment, the invention is directed to a method of securing an expandable medical device for implantation in a body to an expansion member. The method comprises the steps of providing an expansion member having an inner surface and an outer surface, providing an expandable medical device having an inner surface and an outer surface, at least one of the outer surface of the expansion member and the inner surface of the expandable medical device having a pressure sensitive adhesive applied thereto and disposing the expandable medical device about the expansion member and adhering the expandable medical device to the expansion member wherein the expandable medical device in an expanded state releases from the expansion member upon contraction of the expansion member.

In yet another embodiment, the invention is directed to a medical device deliver apparatus comprising a catheter having an expandable and contractible member. The expandable and contractible member is in a contracted state. An expandable medical device is disposed about the expandable and contractible member. The expandable medical device is in an unexpanded state where at least portions of at least one of the medical device and the expandable and contractible member have a pressure sensitive adhesive applied thereto to adhere the medical device to the expandable and contractible member. The pressure sensitive adhesive is selected to release the medical device from the expandable and contractible member upon expansion of the expandable and contractible member from an unexpanded state.

BRIEF DESCRIPTION OF THE SEVERAL VIEWS OF THE DRAWING(S)

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
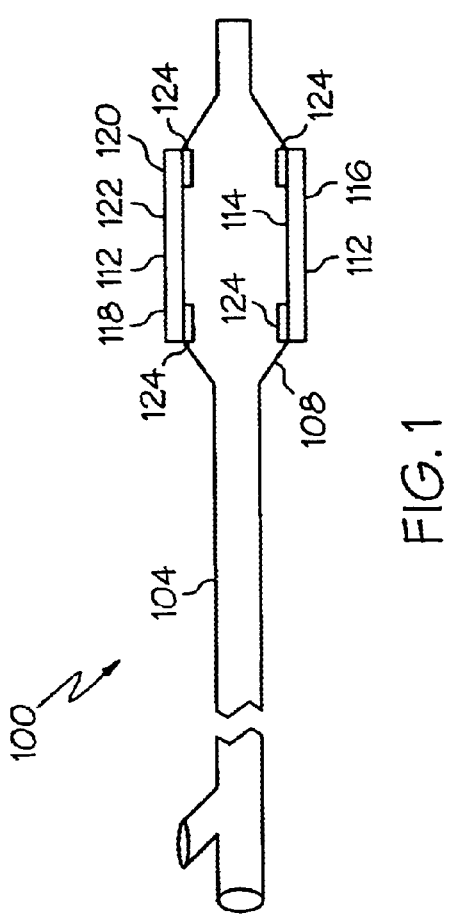
FIG. 1 shows a side elevational cross-sectional view of a medical delivery device with a stent adhered to a medical balloon.

In one embodiment, the instant invention is directed to a stent delivery apparatus such as that shown generally at 100 in FIG. 1. Stent delivery apparatus 100 comprises a catheter 104 having a medical balloon 108 disposed thereabout and an expandable stent 112 disposed about medical balloon 108. An inflation fluid may be supplied to medical balloon 108 via an inflation lumen (not shown). Additional details concerning the construction of suitable stent delivery apparatuses for use in the invention may be found in U.S. Pat. Nos. 6,036,697, 5,893,868 and 5,957,930 and elsewhere in the patent literature. Any suitable stent may be used whether formed of metal or of polymeric material or of another material. Examples of suitable stents are disclosed in copending, commonly assigned U.S. application Ser. No. 08/511076 and U.S. Pat. No. 6,033,433. Medical balloon 108 is capable of being expanded and contracted. Medical balloon 108 may be made of any balloon materials known in the art. Examples of balloon materials may be found in U.S. Pat. Nos. 5,556,383 and 6,024,752. A pressure sensitive adhesive 124 is applied to stent 112 to adhere stent 112 to medical balloon 108. The pressure sensitive adhesive is selected so as to release stent 112 from medical balloon 108 upon contraction of balloon 108.

Figure 2:
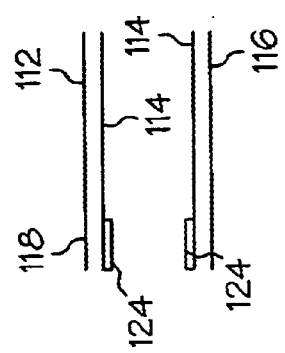
FIG. 2 shows a schematic cross-sectional view of a stent with a pressure sensitive adhesive on the proximal end thereof.
Figure 4:
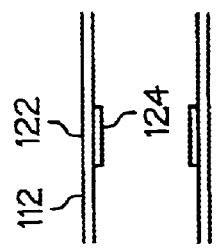
FIG. 4 shows a schematic cross-sectional view of a stent with a pressure sensitive adhesive on the middle portion thereof.
Figure 3:
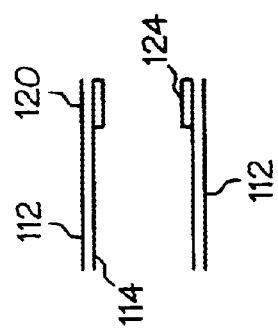
FIG. 3 shows a schematic cross-sectional view of a stent with a pressure sensitive adhesive on the distal end thereof.

As shown in FIG. 1, stent 112 has an inner surface 114 and an outer surface 116, a proximal end 118, a distal end 120 and a middle portion 122. Pressure sensitive adhesive 124 is applied to inner surface 114 of proximal end 118 and distal end 120 of stent 112. The invention also contemplates applying pressure sensitive adhesive 124 only to inner surface 114 of proximal end 118 of stent 112 as shown in FIG. 2. The invention further contemplates applying pressure sensitive adhesive 124 only to inner surface 114 of distal end 120 of stent 112 as shown in FIG. 3. The adhesive may also be applied exclusively to middle portion 122 of stent 112 as shown in FIG. 4. In another embodiment of the invention, pressure sensitive adhesive is applied to the interior surface of at least one of the ends of the stent as well as to the interior of the middle portion of the stent. The pressure sensitive adhesive may also be applied to the entirety of the inner surface of the stent.

Figure 5:
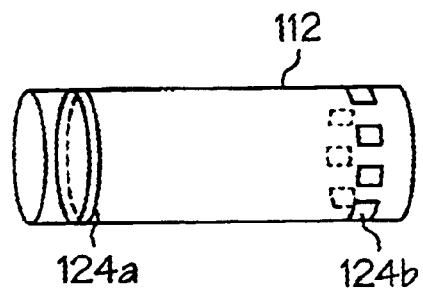
FIG. 5 shows a schematic side view of a stent with a continuous and discontinuous bands of pressure sensitive adhesive thereon.

The pressure sensitive adhesive may be applied to the inner surface of the stent in the form of one or more continuous circumferential bands 124a and/or discontinuous circumferential bands 124b as shown in FIG. 5. Whether a continuous band is achievable depends on the construction of the stent.

Figure 6:
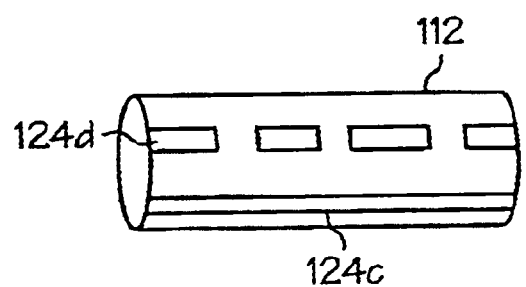
FIG. 6 shows a schematic side view of a stent with a continuous and discontinuous longitudinal strip of pressure sensitive adhesive thereon.

As shown in FIG. 6, the pressure sensitive adhesive may be applied as to the interior surface of the stent in the form of one or more continuous longitudinal strips 124c and/or discontinuous longitudinal strips 124d depending on the design of the stent. The invention also contemplates the application of pressure sensitive adhesive to the interior of the stunt in the form of one or more helical (continuous or discontinuous) strips (not shown).

Figure 7:
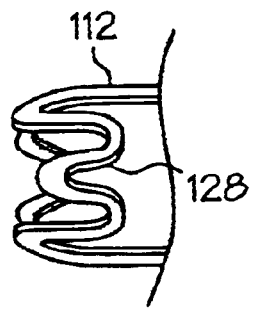
FIG. 7 shows a portion of an end of a stent.

The pressure sensitive adhesive may also be applied to the edges 128 of a stent 112 as shown in FIG. 7.

Desirably, the pressure sensitive adhesive will be applied in a very thin layer to avoid adding to the cross section of the stent. In particular, where the pressure sensitive adhesive is selectively applied to different portions of the stent, it is desirable to provide the pressure sensitive adhesive in a very thin layer so that the stent will present a substantially smooth surface to the balloon.

The invention also contemplates applying the pressure sensitive adhesive to the balloon. The pressure sensitive adhesive should not, however, be applied to the balloon in such a way as to hinder or prevent expansion of the balloon. Desirably, the pressure sensitive adhesive will be applied to the balloon in the unexpanded state after it has been mounted on the catheter and, where the balloon is folded, after it has been appropriately folded. The pressure sensitive adhesive may be applied to the entirety of the balloon or in circumferential bands, spiral patterns or longitudinal strips whether in continuous form or in the form of discontinuous strips of adhesives. The pressure sensitive adhesive may be applied exclusively to one or both ends of the balloon. More generally, the adhesive may be applied to the balloon in any other suitable geometric shape or pattern including any of the patterns disclosed herein for stents. The pressure sensitive adhesive may be applied to the balloon prior to disposing the stent thereabout or while the stent is disposed thereabout. In the latter case, it is desirable to provide the stent with a mask which may be removed after the pressure sensitive adhesive is applied to the balloon.

The pressure sensitive adhesive may be sprayed on to the stent or balloon, painted on or otherwise applied using standard techniques known to one of ordinary skill in the art. Where the adhesive is to be applied to only a portion of the stent or balloon, a mask may optionally be used to limit the application of the adhesive to the desired portion(s) of the stent or balloon.

The invention is also directed more generally toward the use of adhesives to secure a medical device to a balloon using any of the techniques disclosed above. The medical device may be any expandable medical device which is to be released into the body including stents, stent-grafts, grafts, vena cava filters and other filters.

In another embodiment, the invention is directed to an expanded medical device disposed about an expanded expansion member on a catheter where the expanded medical device is adhered to the expanded expansion member via a pressure sensitive adhesive which releases upon contraction of the expansion member. Desirably, the expanded member is a medical balloon. Also desirably, the expanded medical device is a stent. The pressure sensitive adhesive may be present on the expanded member or the medical device or both.

In another embodiment, the invention is directed to a medical device delivery apparatus comprising a catheter having an expandable and contractible member and an expandable medical device disposed about the expandable and contractible member. At least portions of at least one of the medical device and the expandable and contractible member have a pressure sensitive adhesive applied thereto to adhere the medical device to the expandable and contractible member. The pressure sensitive adhesive is selected so as to release the medical device from the expandable and contractible member upon contraction of the member from an expanded state.

Desirably, the expandable and contractible member will be a medical balloon. The invention also contemplates the use of other mechanical devices which are capable of expansion and contraction. Mechanical expansion devices include a spring as disclosed in U.S. Pat. No. 5,211,654 and mechanical expanders as disclosed in U.S. Pat. No. 5,855,565.

The pressure sensitive adhesive, in conjunction with the balloon and stent, must form a bond strong enough to withstand advancement to the desired bodily location and yet release subsequent to inflation when the balloon is deflated. Desirably, the bond formed by the pressure sensitive adhesive will withstand balloon dilation forces. Where bond breakage occurs, as might be expected with folded balloons, the adhesive must be capable of reforming bonds as the balloon expands and once the balloon is fully expanded.

Suitable pressure sensitive adhesives for use in the present invention include silicone type pressure sensitive adhesives, acrylic type pressure sensitive adhesives and polyurethane type pressure sensitive adhesives. Examples of acrylic type pressure sensitive adhesives include NeoTac A-580, NeoTac A-574, NeoTac 2010, NeoTac 2457, NeoTac 2465, NeoTac 5468, all from Zeneca Resins. An example of a polyurethane type pressure sensitive adhesive is NeoTac 560 also from Zeneca Resins. Desirably, the pressure sensitive adhesive will have good water resistance to ensure good adhesion when the stent and balloon are in contact with bodily fluids. Also desirably, the adhesive will be biocompatible. The specific choice of pressure sensitive adhesive will depend on the choice of balloon and stent.

In accordance with the invention, the pressure sensitive adhesive may be applied to the stent in any suitable geometric shape or pattern. The choice of location and pattern for applying the adhesive to the stent or expandable medical device will depend on the medical device delivery apparatus used for delivery of the stent or medical device as well as other factors. In order to maintain maximum control over the stent, the entirety of the stent may be coated with adhesive. In order to maintain control over the stent for as long as possible, it is desirable to apply pressure sensitive adhesive to that portion of the stent which is the last to break contact with the balloon. Whether this location is at the proximal end, the distal end, the middle of the stent, or elsewhere along the stent depends on the construction of the balloon and medical delivery device.

In yet another embodiment, the invention is directed to a method of securing an expandable medical device for implantation in a body to an expansion member. In accordance with the method, an expansion member having an inner surface and an outer surface is provided as is an expandable medical device having an inner surface and an outer surface, with at least one of the outer surface of the expansion member and the inner surface of the expandable medical device having a pressure sensitive adhesive applied thereto. The expandable medical device is disposed about the expansion member and adhered to the expansion member. The expandable medical device in an expanded state releases from the expansion member upon contraction of the expansion member. Desirably, the expandable medical device is a stent, stent-graft, graft, vena cava filter or other filter. Also desirably, the expansion member is a medical balloon.

In yet another embodiment, the invention is directed to a method of delivering an expanded medical device to a desired bodily location. As part of the method, an expanded medical device disposed about an expanded expansion member on a catheter is provided at a desired bodily location. The expanded medical device is adhered to the expanded expansion member via a pressure sensitive adhesive which releases upon contraction of the expansion member. The expansion member is contracted thereby releasing the expanded medical device from the expansion member and the expansion member and catheter withdrawn from the body. Desirably, the expanded medical device is a stent, stent-graft, graft, vena cava filter or other filter. Also desirably, the expansion member is a balloon.

In yet another embodiment, the invention is directed to a medical device deliver apparatus comprising a catheter having an expandable and contractible member. The expandable and contractible member is in a contracted state. An expandable medical device is disposed about the expandable and contractible member. The expandable medical device is in an unexpanded state where at least portions of at least one of the medical device and the expandable and contractible member have a pressure sensitive adhesive applied thereto to adhere the medical device to the expandable and contractible member. The pressure sensitive adhesive is selected to release the medical device from the expandable and contractible member upon expansion of the expandable and contractible member from an unexpanded state.

In use, the medical device (or stent) in the contracted state adheres to the expansion member (or balloon) because of the presence of the pressure sensitive adhesive. As the expansion member expands, some of the bonds between the expansion member and medical device may break. Nevertheless, when the medical device is fully expanded, and prior to contraction of the expansion member, the medical device continues to adhere or, where bonds had been broken during expansion, resumes adhering to the expansion member because of the pressure between the expansion member and the medical device. When the expansion member is contracted in size and ceases to apply pressure to the medical device, all bonds between the expansion member and the medical device break.

In addition to being directed to the embodiments described above and claimed below, the present invention is further directed to embodiments having different combinations of the dependent features described above and/or claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device delivery apparatus comprising:
   a catheter having an expandable and contractible member; and
   an expandable medical device disposed about the expandable and contractible member;
   wherein at least a portion of at least one of the medical device and the expandable and contractible member has a pressure sensitive adhesive applied thereto to adhere the medical device to the expandable and contractible member, the pressure sensitive adhesive selected so as to release the medical device from the expandable and contractible member upon contraction of the member from an expanded state.

2. The medical device delivery apparatus of claim 1 wherein the expandable medical device is a stent.

3. The medical device delivery apparatus of claim 2 wherein the expandable and contractible member is a medical balloon.

4. The medical device delivery apparatus of claim 3 wherein the stent has an inner surface and an outer surface, the inner surface facing the balloon and the pressure sensitive adhesive is applied to the inner surface of the stent.

5. The medical device delivery apparatus of claim 4 wherein the stent has a proximal end and a distal end and the pressure sensitive adhesive is applied to at least one of the proximal and distal ends of the stent.

6. The medical device delivery apparatus of claim 5 wherein the pressure sensitive adhesive is applied only to the proximal end of the stent.

7. The medical device delivery apparatus of claim 5 wherein the pressure sensitive adhesive is applied only to the distal end of the stent.

8. The medical device delivery apparatus of claim 5 wherein the pressure sensitive adhesive is applied only to the proximal and distal ends of the stent.

9. The medical device delivery apparatus of claim 5 wherein the pressure sensitive adhesive is applied only to the proximal and distal ends of the stent and a middle portion of the stent midway between the proximal and distal ends.

10. The medical device delivery apparatus of claim 4 wherein the pressure sensitive adhesive is applied to the entirety of the inner surface of the stent.

11. The medical vice delivery apparatus of claim 4 wherein the stent has a proximal end, a distal end, and a middle portion between the proximal and distal ends, and the pressure sensitive adhesive is applied only to the middle portion of the stent.

12. The medical device delivery apparatus of claim 4 wherein the pressure sensitive adhesive is applied to the stent in the form of circumferential bands.

13. The medical device delivery apparatus of claim 4 wherein the pressure sensitive adhesive is applied to the stent in the form of longitudinal strips.

14. The medical device delivery apparatus of claim 4 wherein the pressure sensitive adhesive is applied to the stent in the form of helical strips.

15. The medical device delivery apparatus of claim 3 wherein the pressure sensitive adhesive is applied to the balloon in an unexpanded state.

16. The medical device delivery apparatus of claim 1 wherein the expandable medical device is selected from the group consisting of stent, stent-grafts, grafts and vena cava filters.

17. A catheter assembly comprising an expanded medical device and an expanded expansion member, said expanded medical device disposed about said expanded expansion member, the expanded medical device adhered to the expanded expansion member via a pressure sensitive adhesive which releases upon contraction of the expansion member.

18. The expanded medical device of claim 17 wherein the expansion member is a medical balloon and the expanded medical device is a stent.

19. The expanded medical device of claim 18 wherein the pressure sensitive adhesive is applied to an inner surface of the stent.

20. A method of securing an expandable medical device for implantation in a body to an expansion member comprising the steps of:
   providing an expansion member having an inner surface and an outer surface;
   providing an expandable medical device having an inner surface and an outer surface, at least one of the outer surface of the expansion member and the inner surface of the expandable medical device having a pressure sensitive adhesive applied thereto; and
   disposing the expandable medical device about the expansion member and adhering the expandable medical device to the expansion member wherein the expandable medical device in an expanded state releases from the expansion member upon contraction of the expansion member.

21. The method of claim 20 wherein the expandable medical device is a stent and the expansion member is a medical balloon.

22. The method of claim 21 wherein the pressure sensitive adhesive is applied to an inner surface of the stent.

23. A method of delivering an expanded medical device to a desires bodily location comprising the steps of:
   providing an expansion member having an inner surface and an outer surface;
   providing an expandable medical device in an unexpanded state having an inner surface and an outer surface, at least one of said outer surface of said expansion member and said inner surface of said expandable medical device having pressure sensitive adhesive applied thereto;
   disposing said expandable medical device about said expansion member said expansion member adhesively secured to said expandable medical device with said pressure sensitive adhesive;
   providing said expansion member and said expandable medical device in an expanded state at a desired body location;

contracting the expansion member thereby releasing the expanded medical device from the expansion member; and withdrawing the expansion member from the body.

24. The method of claim 23 wherein the expanded medical device remains at the desired bodily location.

25. The method of claim 23 wherein the expanded medical device is a stent and the expansion member is a balloon.

26. A stent delivery apparatus comprising:

a catheter having an expandable and contractible member; and an expandable stent disposed about the expandable and contractible member;

wherein at least a portion of at least one of the stent and the expandable and contractible member has a pressure sensitive adhesive applied thereto to adhere the stent to the expandable and contractible member, the pressure sensitive adhesive selected so as to release the stent from the expandable and contractible member upon contraction of the member from an expanded state.

* * * * *

UNITED STATES PATENT AND TRADEMARK OFFICE
CERTIFICATE OF CORRECTION

PATENT NO. : 6,635,078 B1 Page 1 of 1
APPLICATION NO. : 09/667916
DATED : October 21, 2003
INVENTOR(S) : Sheng-Ping Zhong, Steven A. Schultz and Kristian J. Dimatteo It is certified that error appears in the above-identified patent and that said Letters Patent is hereby corrected as shown below:

Column 7, Line 63 claim 11, delete "vice" and insert --device--; and
Column 8, Line 52 claim 23, delete "desires" and insert --desired--.

Signed and Sealed this

Twenty-ninth Day of July, 2008

JON W. DUDAS
*Director of the United States Patent and Trademark Office*